(12) United States Patent
Park

(10) Patent No.: US 11,911,088 B2
(45) Date of Patent: Feb. 27, 2024

(54) SMOKE PENCIL WITH SWIVEL DEVICE

(71) Applicant: BIO-PROTECH INC., Wonju-si (KR)

(72) Inventor: Ik Ro Park, Irvine, CA (US)

(73) Assignee: BIO-PROTECH INC., Wonju-si (KR)

( * ) Notice: Subject to any disclaimer, the term of this patent is extended or adjusted under 35 U.S.C. 154(b) by 590 days.

(21) Appl. No.: 17/015,958

(22) Filed: Sep. 9, 2020

(65) Prior Publication Data

US 2022/0071688 A1 Mar. 10, 2022

(51) Int. Cl.
*A61B 18/14* (2006.01)
*A61B 18/00* (2006.01)

(52) U.S. Cl.
CPC ...... *A61B 18/1402* (2013.01); *A61B 2018/00607* (2013.01); *A61B 2018/00916* (2013.01); *A61B 2018/1412* (2013.01); *A61B 2218/008* (2013.01)

(58) Field of Classification Search
CPC ...... A61B 18/1402; A61B 2018/00607; A61B 2018/00916; A61B 2018/1412; A61B 2218/008
See application file for complete search history.

(56) References Cited

U.S. PATENT DOCUMENTS

| 2009/0018539 A1* | 1/2009 | Cosmescu ......... A61M 39/1055 606/41 |
| 2018/0243026 A1* | 8/2018 | Park .................. A61B 18/1402 |

FOREIGN PATENT DOCUMENTS

KR 10-2001-0035322 A 5/2001

\* cited by examiner

*Primary Examiner* — Eun Hwa Kim
*Assistant Examiner* — Catherine Premraj
(74) *Attorney, Agent, or Firm* — Studebaker & Brackett PC

(57) ABSTRACT

Proposed is a smoke pencil with swivel device, in which first end portions of first and second cases are rotatably coupled to a body and second end portions of the first case and the second case are inclined downward, so when a user rotates the body, a cable and a suction hose are guided downward. Accordingly, there is an effect that a user can easily rotate the body.

8 Claims, 8 Drawing Sheets

SMOKE PENCIL WITH SWIVEL DEVICE

BACKGROUND OF THE INVENTION

Field of the Invention

The present invention relates to a smoke pencil with swivel device and, more particularly, to a smoke pencil with swivel device that guides a cable and a suction hose downward when a user rotates a body of the smoke pencil with swivel device.

Description of the Related Art

In general, a smoke pencil is representative medical equipment that is used to cut a portion of a tissue of a human body or coagulate a tissue or blood using electricity instead of scalpels usually in surgical operations.

Such a smoke pencil, which uses a principle that a high-frequency current generates a short spark or heat without electrically shocking or stimulating on muscles when flowing through a human body, cuts a desired tissue using high-frequency energy of about 100° C. or coagulates a desired tissue using high-frequency energy of about 60° C.

FIG. 1 is a view showing a smoke pencil of the related art. Referring to FIG. 1, a smoke pencil of the related art, which has been disclosed in Korean Patent Application Publication No. 10-2001-0035322, includes a suction cannula 50, a scalpel 70 coupled to an end of the suction cannula 50 to be heated by high-frequency energy, and a supporting tube 40 coupled to another end of the suction cannula 50. A cable 20 and a suction hose 30 are exposed out of the suction cannula 50 through the supporting tube 40. The cable 20 and the suction hose 30 exposed in this way are connected to an external device 10. A odor suctioned through the suction cannula 50 is discharged to the external device 10 through the suction cannula 50, and the scalpel 70 receiving high-frequency energy from the external device 10 connected with the cable 20 is used for cutting or homeostasis.

Meanwhile, a user rotates and uses a smoke pencil at various angles while performing an operation using the smoke pencil, depending on the shapes of affected parts. Since the external device 10 is fixed at one side of the operating room even if the smoke pencil is rotated, the cable 20 and the suction hose 30 exposed out of the supporting tube 40 have to face the external device 10. However, the smoke pencil has no specific configuration that guides the cable 20 and the suction hose 30 exposed out of the supporting tube 40 toward the external device 10, so there is a problem that a user has difficulty in rotating the smoke pencil.

SUMMARY OF THE INVENTION

The present invention has been made in an effort to solve the problems and an objective of the present invention is to provide a smoke pencil with swivel device that enables a user to easily rotate a body of the smoke pencil with swivel device by guiding a cable and suction hose downward when the user rotates the body.

In order to achieve the objectives of the present invention, a smoke pencil with swivel device includes: a body longitudinally elongated, having a space longitudinally formed therein, having a blade disposed at a longitudinal front of the space to be exposed outside, and having a coupling portion protruding from a longitudinal rear of the space; an operation part including a substrate disposed at a side of the space and electrically connected with the blade, an operator connected to the substrate and exposed over the space, and a cable having an end electrically connected to the substrate and another end extending out of the body through the space and the coupling portion; and a rotation guide including a first case rotatably disposed on a side of an outer surface of the coupling portion, a second case rotatably disposed on another side of the outer surface of the coupling portion and combined with the first case, an inflow air cannula sealing a joint between a side of the coupling portion and first case and a joint between another side of the coupling portion and the second case.

A first end portion of the first case may cover a side of the outer surface of the coupling portion and a second end portion of the first case may be bent downward; and a first end portion of the second case may cover another side of the outer surface of the coupling portion and a second end portion of the second case may be bent downward.

A rotation guide protrusion may be formed on the outer surface of the coupling portion; a first rotation guide slit may be formed on an inner surface of the first case so that a side of the rotation guide protrusion is inserted therein, and a second rotation guide slit may be formed on an inner surface of the second case so that another side of the rotation guide protrusion is inserted therein; and when the body is rotated, the rotation guide protrusion may be rotated in the first rotation guide slit and the second rotation guide slit.

An outer surface of the rotation guide protrusion may slide in contact with an inner surface of the first rotation guide slit and an inner surface of the second rotation guide slit.

The rotation guide protrusion may protrude from an outer surface of a longitudinal end portion of the coupling portion and a rotation support protrusion may protrude from an outer surface of another longitudinal end portion; the first rotation guide slit may be formed an inner surface of a longitudinal portion of the first case and a first rotation support slit may be formed on an inner surface of another longitudinal portion of the first case so that a side of the rotation support protrusion is inserted therein; and the second rotation guide slit may be formed an inner surface of a longitudinal portion of the second case and a second rotation support slit may be formed on an inner surface of another longitudinal portion of the second case so that another side of the rotation support protrusion is inserted therein.

A plurality of shaved portions may be formed inward from a predetermined circumference of the rotation support protrusion on an outer surface of the rotation support protrusion, and when the outer surface of the rotation support protrusion is positioned to come in contact with an inner surface of the first rotation support slit and an inner surface of the second rotation support slit, the shaved portions may be spaced part from the inner surface of the first rotation support slit and the inner surface of the second rotation support slit.

The inflow air cannula tube may have an insertion portion formed in a rod shape to be inserted into the coupling portion, and a bending portion bending toward the first case and the second case at a rear end of the insertion portion positioned outside the coupling portion.

A first guide groove may be formed on an inner surface of the first case so that a side of an outer surface of the bending portion is inserted therein, a second guide groove may be formed on an inner surface of the second case so that another side of the outer surface of the bending portion is inserted therein, and the outer surface of the bending portion may be in contact with an inner surface of the first guide groove and an inner surface of the second guide groove.

A contact portion may protrude from a front end of the insertion portion positioned in the coupling portion to be in contact with an inner surface of the coupling portion, and an outer surface of the insertion portion inserted in the coupling portion may be spaced apart from the inner surface of the coupling portion.

The contact portion may be tapered as the contact portion goes away from the insertion portion.

An inclined portion protruding away from a rear end of the insertion portion may be formed at the rear end of the insertion portion, the bending portion may be formed at an end of the inclined portion that is farthest from the rear end of the insertion portion, the inclined portion may increase in diameter as the inclined portion goes away from the rear end of the insertion portion, and the inclined portion may not be inserted in the first guide groove and the second guide groove so that the rear end of the insertion portion and the first and second grooves are spaced apart from each other.

A first end portion of the first case and a first end portion of the second case may be coupled to the coupling portion, a second end portion of the first case and a second end portion of the second case may be inclined downward, a first wire guide protrusion may be formed on an inner surface between the first end portion and the second end portion of the first case, a second wire guide protrusion may be formed on an inner surface between the first end portion and the second end portion of the second case to be in contact with the first wire guide protrusion, and when the cable is disposed between the first case and the second case, the cable may be placed over the first wire guide protrusion and the second wire guide protrusion and guided out of the first case and the second case.

According to the present invention, since the first end portions of the first and second cases are rotatably coupled to a body and second end portions of the first case and the second case are inclined downward, when a user rotates the body, a cable and a suction hose are guided downward. Accordingly, there is an effect that a user can easily rotate the body.

Further, when the body is rotated, the rotation guide protrusion and the rotation support protrusion are rotated in the first and second rotation guide slits and the first and second rotation support slits, so there is an effect that the coupling portion is stably rotated while being firmly supported inside the first and second cases.

Further, since external air cannot flow into the space defined by the first and second cases, the space defined by the first and second cases is maintained at a predetermined negative pressure, so there is an effect that the smoke moving toward the first and second cases through the coupling portion is easily discharged outside from the first and second cases.

Further, since the rotation support protrusion has the shaved portions, the friction between the rotation support protrusion and the first and second rotation support slits decreases, so there is an effect that the rotation support protrusion is easily inserted while being guided by the first and second rotation support slits.

Further, since the bending portion is fitted in the first and second guide grooves, the smoke flowing to the space defined by the first and second cases through the coupling portion is prevented from leaking outside through between the bending portion and the first and second guide grooves, and air outside the first and second guide grooves is prevented from flowing into the space defined by the first and second cases through between the bending portion and the first and second guide grooves.

Further, since the insertion portion has the contact portion and the inclined portion so that the outer surface of the insertion portion and the inner surface of the coupling portion are spaced apart from each other, there is no friction between the insertion portion and the coupling portion, so there is an effect that the coupling portion is easily rotated.

Further, since the cable guided in the space defined by the first and second cases is placed over the first and second wire guide protrusions, there is no friction between the cable and the inner surfaces of the first and second cases, so there is an effect that the cable is easily moved in the space defined by the first and second cases.

BRIEF DESCRIPTION OF THE DRAWINGS

The above and other objects, features and other advantages of the present invention will be more clearly understood from the following detailed description when taken in conjunction with the accompanying drawings, in which.

DETAILED DESCRIPTION OF THE INVENTION

Hereinafter, a smoke pencil with swivel device according to an exemplary embodiment of the present invention is described in detail with reference to the accompanying drawings.

Figure 1:
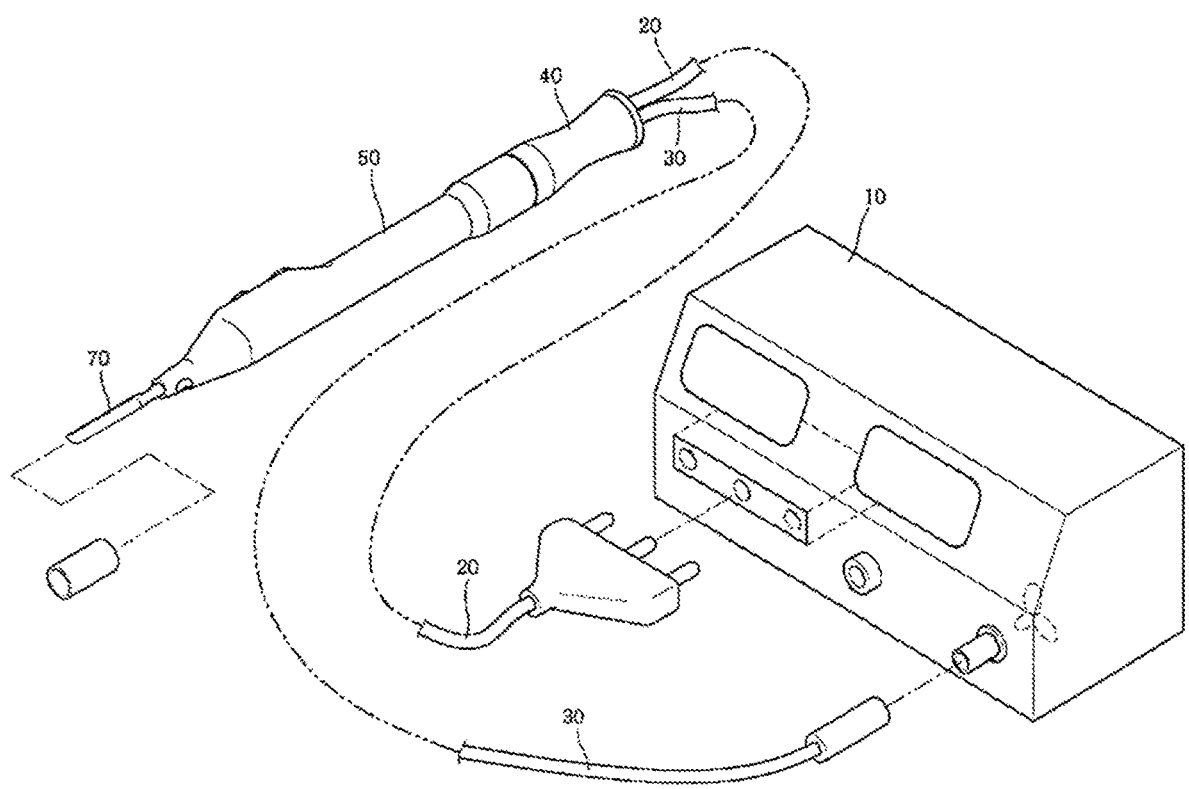
FIG. 1 is a view showing a smoke pencil of the related art.
Figure 2:
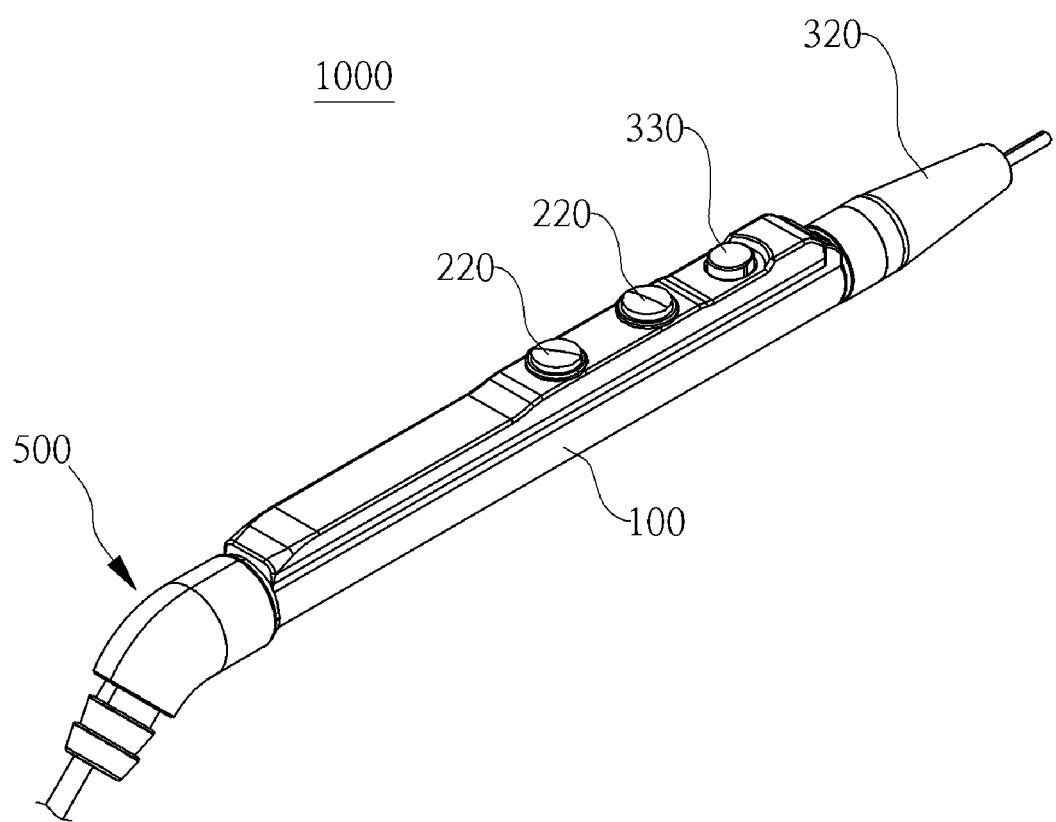
FIG. 2 is a view schematically showing a smoke pencil with swivel device according to an exemplary embodiment of the present invention.
Figure 3:
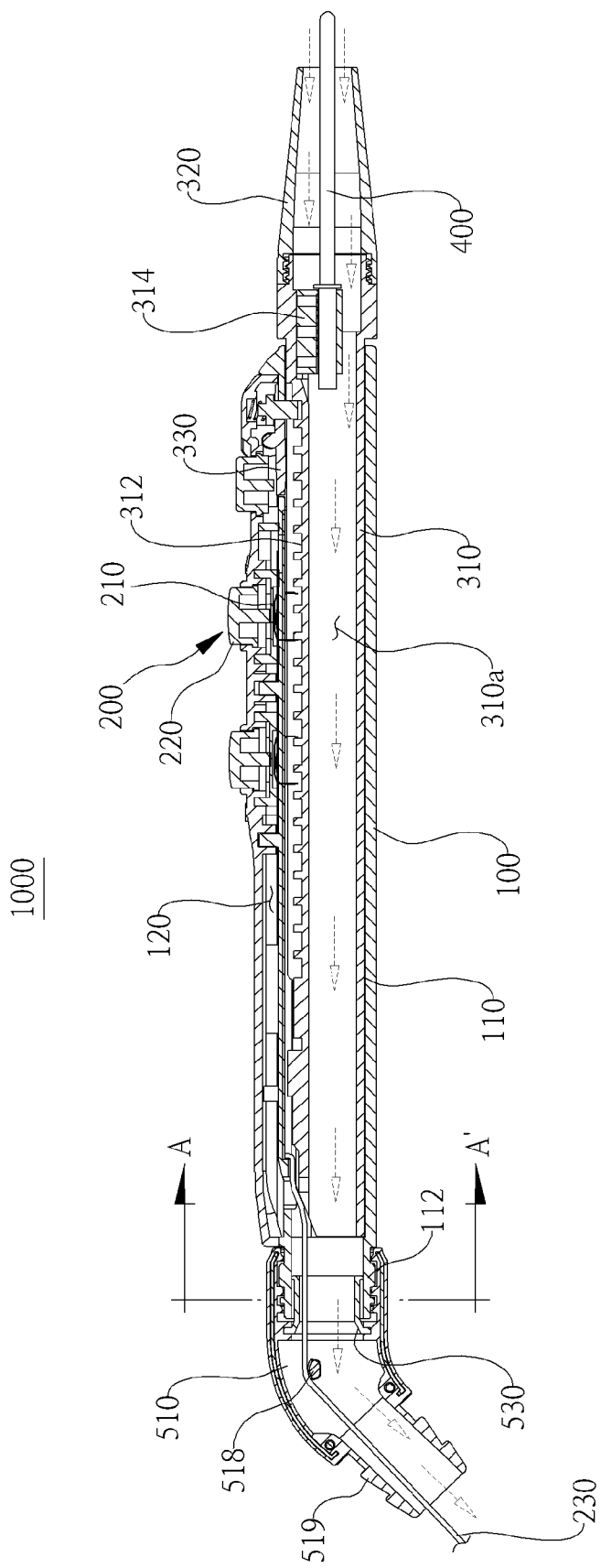
FIG. 3 is a view schematically showing a cross-section of the smoke pencil with swivel device according to an exemplary embodiment of the present invention.

FIG. 2 is a view schematically showing a smoke pencil with swivel device according to an exemplary embodiment of the present invention and FIG. 3 is a view schematically showing a cross-section of the smoke pencil with swivel device according to an exemplary embodiment of the present invention.

Referring to FIGS. 2 and 3, a smoke pencil with swivel device 1000 having a rotation guide according to an exemplary embodiment of the present invention, which is used for a user such as a doctor to cut a portion of a tissue of the patient's body or coagulate blood, includes a body 100, an operation part 200, a stretcher 300, a blade 400, and a rotation guide 500.

Hereafter, unless specifically stated, when a user holds the body 100 with a hand and cuts or coagulates a tissue of a patient's body using the blade 400, the side close to the tissue is referred to as 'forward' or 'front' and the opposite side is referred to as 'rearward' or 'rear'.

The body 100 is a part that a user holds with a hand, is longitudinally elongated, and has a lower space 110 and an upper space 120 positioned over the lower space 110. The lower space 110 and the upper space 120 are separated as independent spaces. The lower space 110 suctions smoke produced when a tissue of a patient's body is cut or coagulated by the blade 400, and the suctioned smoke flows in the lower space 110. The blade 400 is exposed outside through the longitudinal front of the lower space 110 and a coupling portion 112 protrudes from the longitudinal rear of the lower space 110. The upper space 120 provides a space in which a substrate 210 to be described below is disposed.

The operation part 200 includes the substrate 210, an operator 220, and a cable 230. The substrate 210 may be, for example, a Printed Circuit Board (PCB), is disposed in the upper space 120, is electrically connected with the blade 400, and transmits high-frequency energy to the blade 400. The operator 220, for example, may be one or more buttons or touch panels and has a bottom connected to the substrate 210 and a top exposed over the upper space 120. When a user operates the top of the operator 220 exposed upward from the upper space 120, the substrate 210 adjusts the amount of high-frequency energy received from the outside and then transmits the high-frequency energy to the blade 400. The cable 230 may be a wire, etc., and has an end electrically connected to the rear of the substrate 210 and another end extending out of the body 100 through the rear of the lower space 110 and the coupling portion 112. The cable 230 extending out of the body 100 is connected to an external high-frequency generator (not shown) and transmits high-frequency energy generated by the high-frequency generator to the substrate 210.

The stretcher 300 includes a slider 320, an extension 320, a button stopper 330, and a contact guide (not shown). The slider 310 has a long shape to form a suction channel 310a through which smoke is suctioned, and can slide in the lower space 110. The slider 310 has locking steps 312 and a coupling guide 314. The locking steps 312 are recessed and longitudinally arranged on the top of the slider 310. The coupling guide 314 is disposed at the front of the suction channel 310a in the slider 310 and is made of a conductive material, and the blade 400 is coupled to the coupling guide 314. The extension 320 is coupled to the front of the slider 310. The button stopper 330 is supported at the front portion of the upper space 120 and is moved up and down to be locked to or unlocked from the locking steps 312. The contact guide has a side electrically connected to the substrate 210 and another side electrically connected to the coupling guide 314, thereby electrically connecting substrate 210 and the blade 400 to each other. When the button stopper 330 is positioned to be unlocked from the locking step 312 by a user, the slider 310 can slide through the lower space 110, and when the button stopper 330 is locked to the locking step 312, the slider 310 is fixed in the lower space 110. It is possible to adjust the length of the entire body 100 by controlling the length of the slider 310 protruding forward from the lower space 110 using the button stopper 330. The stretcher 300 may be omitted, if necessary. In this case, the coupling guide 314 may be disposed at the front of the lower space 110.

The blade 400 is longitudinally elongated and has an end coupled to the coupling guide 314 and electrically connected with the substrate 210 and another end extending forward from the suction channel 310a to be exposed forward out of the extension 320. When high-frequency energy is transmitted from the substrate 210 to the blade 400, the blade 400 cuts or coagulates a portion of a tissue of a patient's body using the high-frequency energy. When the blade 400 cuts or coagulates a portion of a tissue of a human body, smoke spreading around the blade 400 is suctioned into the suction channel 310a and then discharged outside through the rotation guide 500.

The rotation guide 500 is rotatably coupled to the coupling portion 112. An external suction hose (not shown) is connected to a connection tube 519 of the rotation guide 500. The suction hose is connected to a suction device such as a smoke evacuator that suctions air, so the smoke spreading around the blade 400 in an operation is suctioned into the suction channel 310a and then suctioned into the suction device through the rotation guide 500 and the suction hose.

Since the rotation guide 500 is connected to the suction hose, when a user performs an operation while rotating the body 100 at several angles in accordance with the shape of an affected part, the body 100 should be easily rotated while supported by the rotation guide 500. Further, since the smoke suctioned in the body 100 moves to the rotation guide 500 and is then suctioned into the suction device, the smoke moving to the rotation guide 500 through the body 100 should not leak out of the rotation guide 500. The detailed structure of the rotation guide 500 is described in priority of this configuration.

Figure 4:
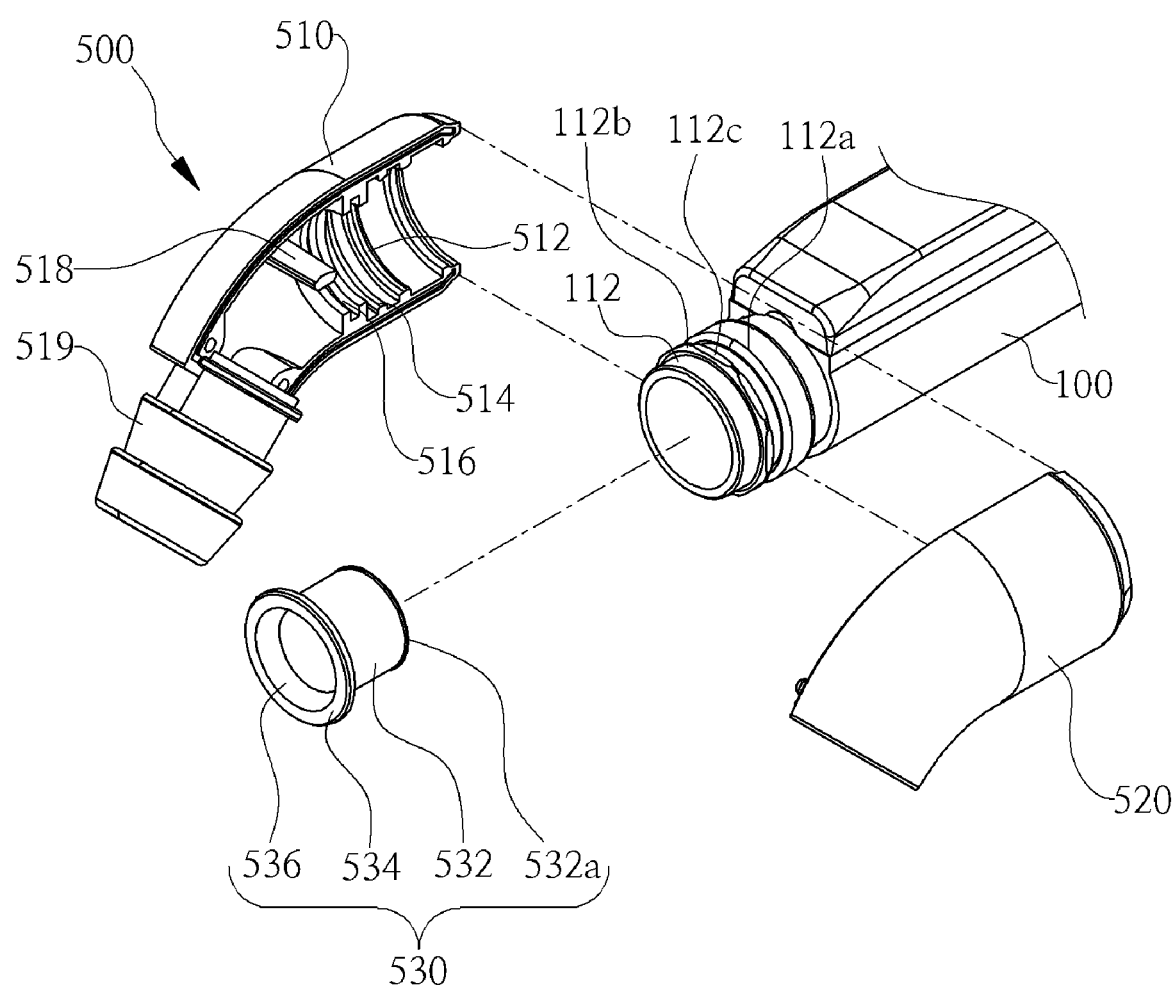
FIG. 4 is an exploded view showing a rotation guide of the smoke pencil with swivel device according to an exemplary embodiment of the present invention seen from a side.
Figure 5:
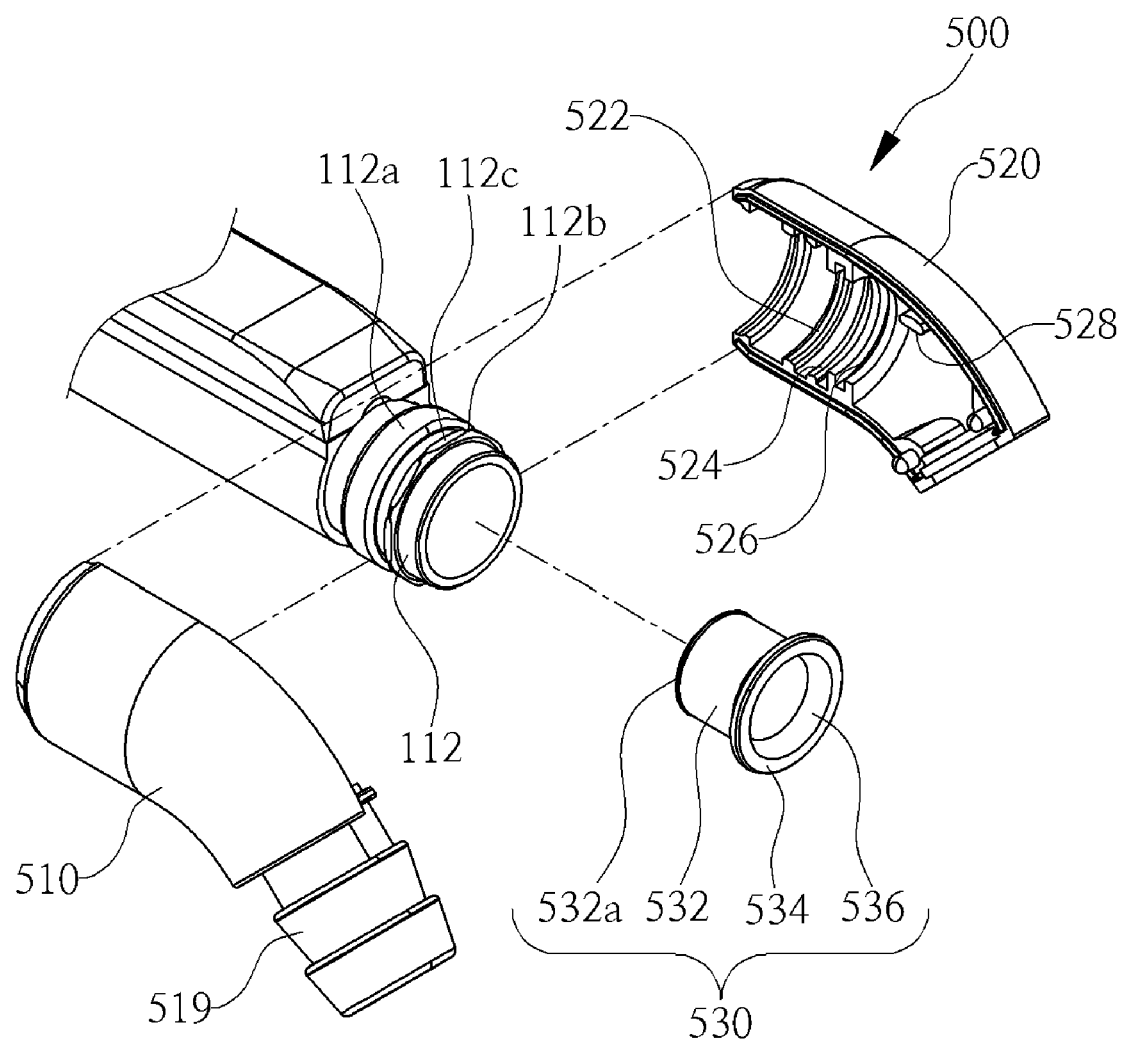
FIG. 5 is an exploded view showing the rotation guide of the smoke pencil with swivel device according to an exemplary embodiment of the present invention seen from another side.
Figure 6:
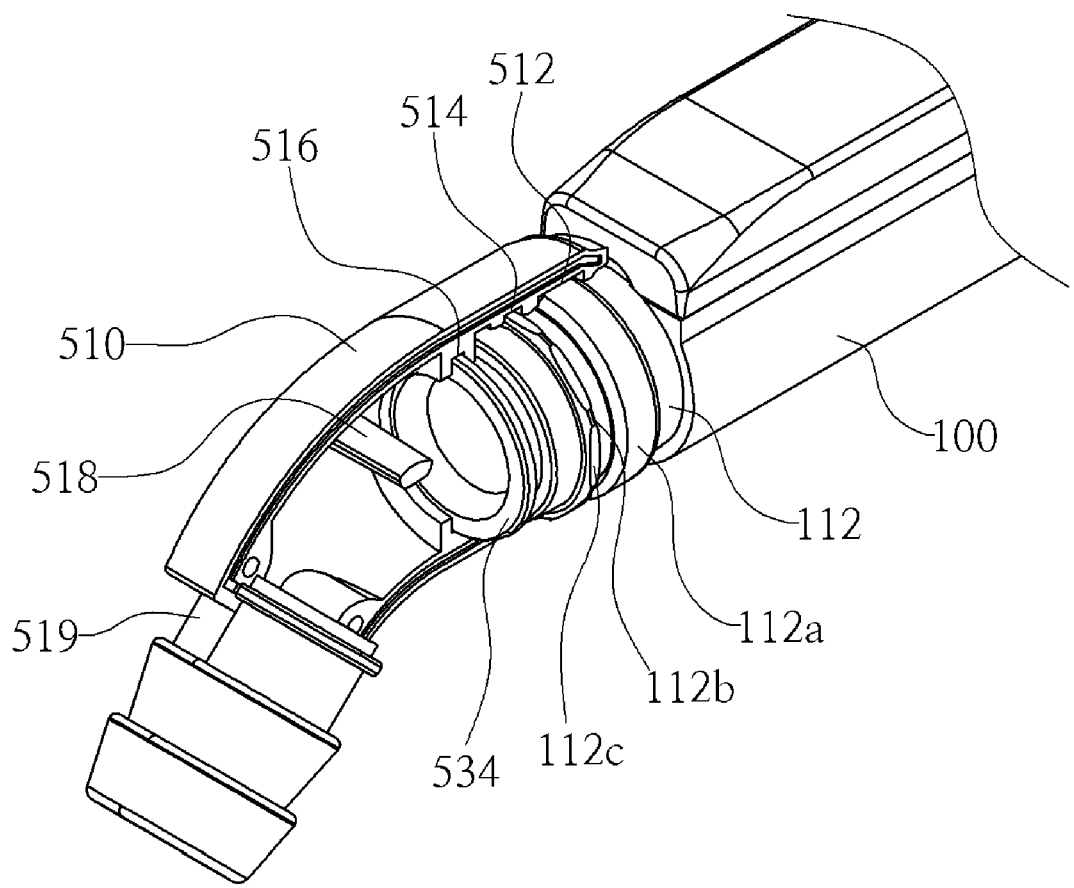
FIG. 6 is a view showing a combination of the rotation guide and a body of the smoke pencil with swivel device according to an exemplary embodiment of the present invention.

FIG. 4 is an exploded view showing a rotation guide of the smoke pencil with swivel device according to an exemplary embodiment of the present invention seen from a side, FIG. 5 is an exploded view showing the rotation guide of the smoke pencil with swivel device according to an exemplary embodiment of the present invention seen from another side, and FIG. 6 is a view showing a combination of the rotation guide and a body of the smoke pencil with swivel device according to an exemplary embodiment of the present invention.

Referring to FIGS. 4 to 6, the coupling portion 112 having a cylindrical shape integrally protrudes from the rear of the body 100 and the inside of the coupling portion 112 communicates with the lower space 110. A rotation guide protrusion 112a protrudes in a ring shape from the outer surface of the longitudinal front portion of the coupling portion 112 and a rotation support protrusion 112b protrudes in a ring shape from the outer surface of the longitudinal rear portion of the coupling portion 112.

The rotation guide 500 includes a first case 510, a second case 520, and an inflow air cannula 530. The inflow air cannula 530 will be described with reference to FIG. 8.

The first case 510 is provided to cover a side of the outer surface of the coupling portion 112. The second case 520 is provided to cover another side of the outer surface of the coupling portion 112. The sides facing each other of the first case 510 and the second case 520 are fitted to each other. In order to guide coupling to the coupling portion 112, a first rotation guide slit 512 is formed on the inner surface of the longitudinal front portion of the first case 510 so that a side of the rotation guide protrusion 112a is inserted therein, and a first rotation support slit 514 is formed on the inner surface of the longitudinal rear portion of the first case 510 so that a side of the rotation support protrusion 112b is inserted therein. A second rotation guide slit 522 is formed on the outer side of the longitudinal front portion of the second case 520 so that another side of the rotation guide protrusion 112a is inserted therein, and a second rotation support slit 524 is formed on the inner surface of the longitudinal rear portion of the second case 520 so that another side of the rotation support protrusion 112b is inserted therein. Since the coupling portion 112 has the rotation guide protrusion 112a and the rotation support protrusion 112b, when the body 100 is rotated, the rotation guide protrusion 112a and the rotation support protrusion 112b are rotated in the first and second rotation guide slits 512 and 522 and the first and second rotation support slits 514 and 524, so there is an effect that the coupling portion 112 is stably rotated while being firmly supported inside the first and second cases 510 and 520.

Further, since first end portions of the first and second cases 510 and 520 are rotatably coupled to the body 100 and second end portions of the first and second cases 510 and 520 are inclined downward, when a user rotates the body 100, the cable 230 and the suction hose are guided downward through the second end portions of the first and second cases 510 and 520. Accordingly, there is an effect that the user can easily rotate the body 100.

When the first and second cases 510 and 520 are coupled to the coupling portion 112, the outer surface of the rotation guide protrusion 112a comes in contact with the inner surfaces of the first rotation guide slit 512 and the second rotation guide slit 522. Accordingly, when the body 100 is rotated, the rotation guide protrusion 112a slides and rotates in contact with the inner surfaces of the first rotation guide slit 512 and the second rotation guide slit 522. Therefore, there is an effect that the rotation guide protrusion 112a is stably rotated while being guided by the inner surfaces of the first rotation guide slit 512 and the second rotation guide slit 522.

Further, since the outer surface of the rotation guide protrusion 112a is in contact with the inner surfaces of the first and second rotation guide slits 512 and 522, external air cannot come into the spaced defined by the first and second cases 510 and 520 through the space between the first and second rotation guide slits 512 and 522, so the inside defined by the first and second cases 510 and 520 is maintained at a predetermined negative pressure. Accordingly, there is an effect that the smoke moving toward the first and second cases 510 and 520 through the coupling portion 112 is easily discharged outside from the first and second cases 510 and 520.

Figure 7:
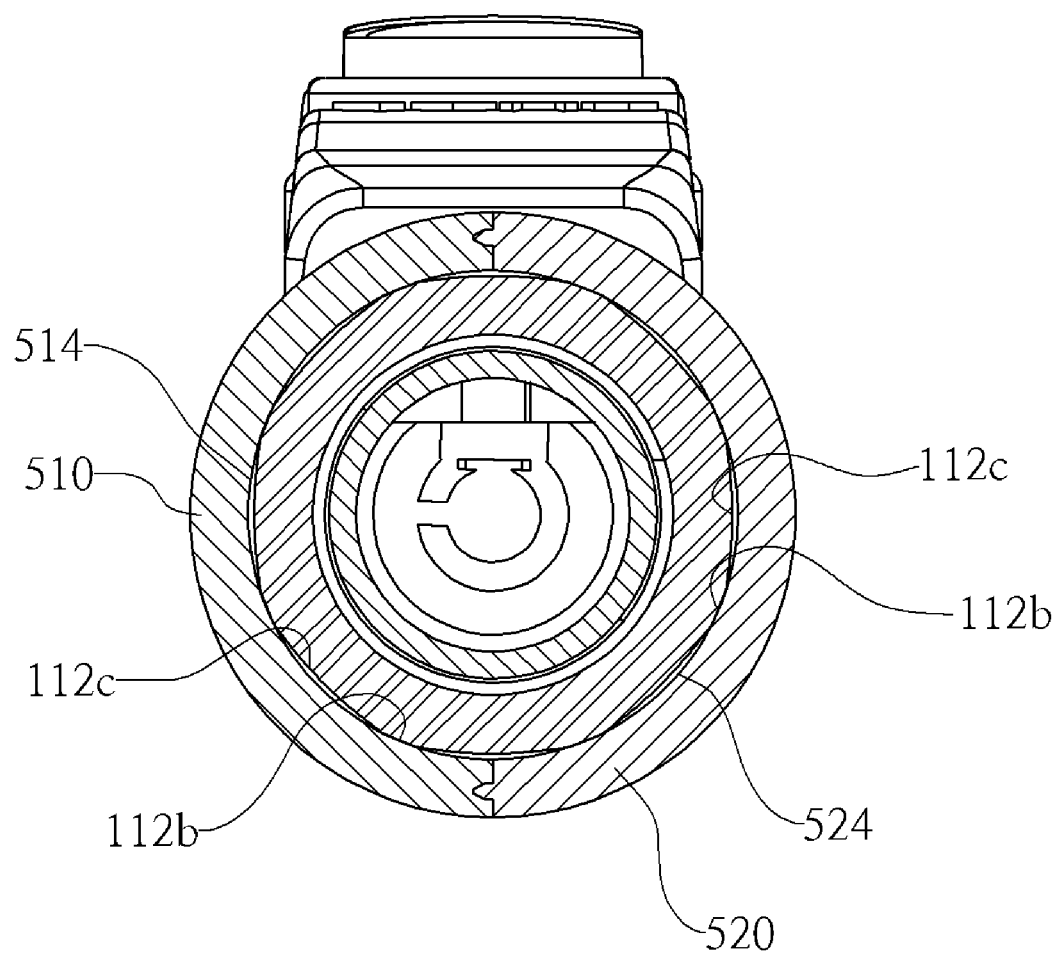
FIG. 7 is a cross-sectional view taken along line A-A' of FIG. 3.

FIG. 7 is a cross-sectional view taken along line A-A' of FIG. 3.

Referring to FIGS. 6 and 7, a plurality of shaved portions 112c is formed inward from a predetermined circumference of the rotation support protrusion 112b on the outer surface of the rotation support protrusion 112b. The shaved portions 112c are positioned inward from the predetermined circumference of the rotation support protrusion 112b. Accordingly, when the outer surface of the rotation support protrusion 112b is rotated on the inner surfaces of the first and second rotation support slits 514 and 524 by rotation of the coupling portion 112 after the rotation support protrusion 112b is inserted in the first and second rotation support slits 514 and 524, the shaved portions 112c do not come in contact with the inner surfaces of the first and second rotation support slits 514 and 524. Accordingly, the contact area between the outer surface of the rotation support protrusion 112b and the inner surfaces of the first and second rotation support slits 514 and 524 decreases, so friction between the rotation support protrusion 112b and the first and second rotation support slits 514 and 524 is reduced. As described above, since friction between the rotation support protrusion 112b and the first and second rotation support slits 514 and 524 is reduced, there is an effect that the rotation support protrusion 112b is more easily rotated while being guided by the first and second rotation support slits 514 and 524.

Figure 8:
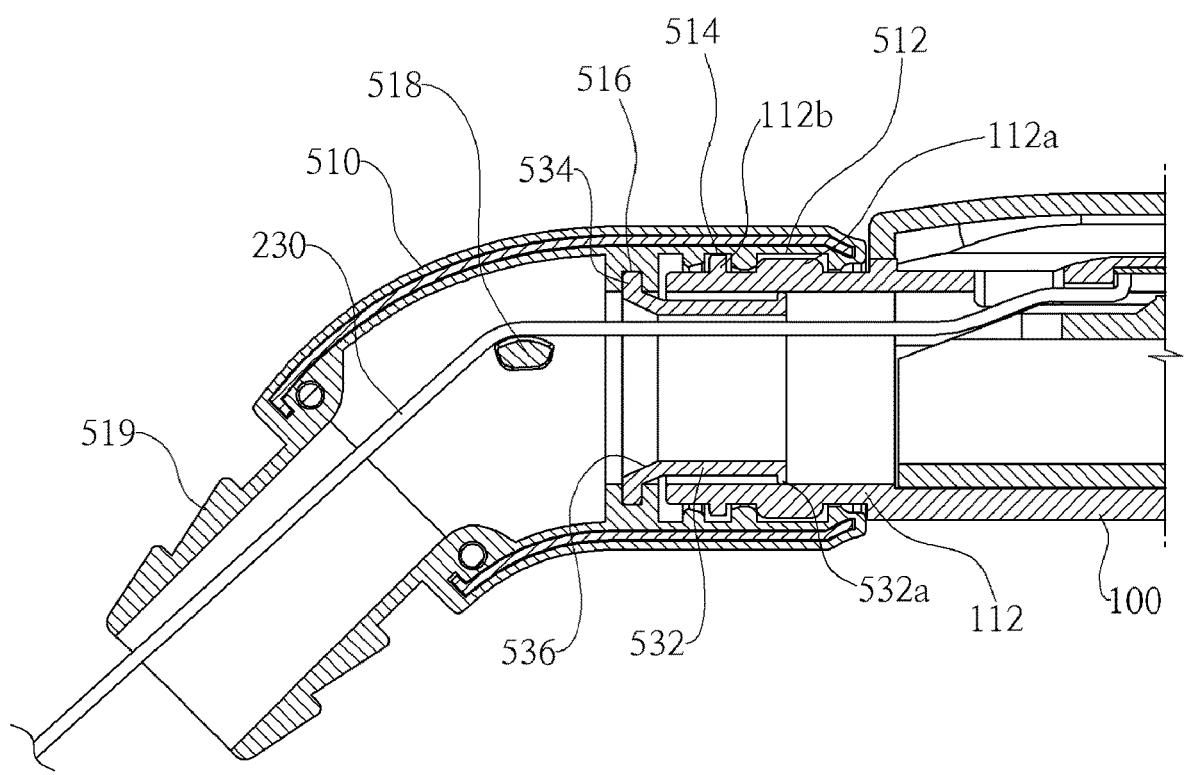
FIG. 8 is a cross-sectional view showing a combination of the rotation guide and a body of the smoke pencil with swivel device according to an exemplary embodiment of the present invention.

FIG. 8 is a cross-sectional view showing a combination of the rotation guide and a body of the smoke pencil with swivel device according to an exemplary embodiment of the present invention.

Referring to FIGS. 4 to 8, the inflow air cannula 530 prevents fluid from flowing between a side of the coupling portion 112 and the first case 510 and between another side of the coupling portion 112 and the second case 520. In detail, the inflow air cannula 530 prevents smoke flowing through the coupling portion 112 from leaking outside while the smoke flows through the space defined between the first and second cases 510 and 520, and prevents air outside the first and second cases 510 and 520 from flowing into the space defined by the first and second cases 510. The inflow air cannula 530 has an insertion portion formed in a rod shape to be inserted into the coupling portion 112 and a bending portion 534 bending toward the first case 510 and the second case 520 at the rear end of the insertion portion 532 positioned outside the coupling portion 112. An inclined portion 536 protruding away from the rear end of the insertion portion 532 is formed at the rear end of the insertion portion 532 and the bending portion 534 may be formed at the end of the inclined portion 536 that is farthest from the rear end of the insertion portion 532. The inclined portion 536 increases in diameter as it goes away from the rear end of the insertion portion 532.

A first guide groove 516 is formed on the inner surface of the first case 510 so that a side of the outer surface of the bending portion 534 is inserted therein, and a second guide groove 526 is formed on the inner surface of the second case 520 so that another side of the outer surface of the bending portion 534 is inserted therein. When the first and second cases 510 and 520 are coupled to the coupling portion 112 after the insertion portion 532 is inserted in the coupling portion 112, the bending portion 534 is inserted into the first and second guide grooves 516 and 526, so the outer surface of the bending portion 534 comes in contact with the inner surface of the first guide groove 516 and the inner surface of the second guide groove 526.

As described above, since the bending portion 534 is fitted in the first and second guide grooves 516 and 526, smoke flowing to the space defined by the first and second cases 510 and 520 through the coupling portion 112 is prevented from leaking outside through between the bending portion 534 and the first and second guide grooves 516 and 526 and air outside the first and second guide grooves 516 and 526 is prevented from flowing into the space defined by the first and second cases 510 and 520 through between the bending portion 534 and the first and second guide grooves 516 and 526.

A contact portion 532a may protrude from the front end of the insertion portion 532 positioned in the coupling portion 112. The contact portion 532a spaces the insertion portion 532 apart from the coupling portion 112 to prevent friction between the insertion portion 532 and the coupling portion 112. That is, the larger the contact area between the coupling portion 112 and the insertion portion 532 inserted in the coupling portion 112, the larger the friction between the insertion portion 532 and the coupling portion 112. Further, the larger the friction between the insertion portion 532 and the coupling portion 112, the more the rotation of the coupling portion 112 is limited. The protrusive contact portion 532a is formed at the front end of the insertion portion 532 to solve this problem in the present invention. Since the outer surface of the insertion portion 532 and the inner surface of the coupling portion 112 are spaced apart from each other by the contact portion 532a, there is no friction between the insertion portion 532 and the coupling portion 112, so there is an effect that the coupling portion 112 is easily rotated. The contact portion 532 may be tapered as it goes away from the insertion portion 532 to minimize the contact area between the contact portion 532a and the coupling portion 112.

The inclined portion 536 is not inserted in the first guide groove 516 and the second guide groove 526 so that the rear end of the insertion portion 532 and the first and second guide grooves 516 and 526 are spaced part from each other. The inclined portion 536 has a similar function to the contact portion 532a, so the rear end of the insertion portion 532 and the first and second guide grooves 516 and 526 are spaced part from each other by the inclined portion 536. Accordingly, there is an effect that there is no friction between the insertion portion 532 and the first and second guide grooves 516 and 526, and the coupling portion 112 is more easily rotated.

Meanwhile, the smoke moving from the coupling portion 112 to the rotation guide 500 is suctioned into the suction device (not shown) through the suction hose (not shown). To this end, for example, the connection tube 519 protrudes from an end of the first case 510 and the suction hose is connected to the connection tube 519. The cable 230 guided inside the first and second cases 510 and 520 from the coupling portion 112 is guided out of the first and second case 510 and 520, that is, toward the suction hose through the connection tube 519. Since the suction hose is usually elongated downward due to gravity, the first and second cases 510 and 520 are bent downward to be easily coupled to the suction hose. In detail, the front portion of the first case 510 covers a side of the outer surface of the coupling portion 112 and the rear portion of the first case 510 is smoothly curved in a predetermined direction. Similarly, the front portion of the second case 520 covers another side of the outer surface of the coupling portion 112 and the rear portion of the second case 520 is smoothly curved in a predetermined direction.

A first wire guide protrusion 518 is formed at the center portion on the inner surface between an end and another end of the first case 510. Similarly, a second wire guide protrusion 528 that is in contact with the first wire guide protrusion 518 is formed at the center portion on the inner surface between an end and another end of the second case 520. When the cable 230 is disposed between the first case 510 and the second case 520, the cable 230 is placed over the first wire guide protrusion 518 and the second wire guide protrusion 528 and guided out of the first case 510 and the second case 520. When the cable 230 is guided inside the first and second case 510 and 520 and placed over the first and second wire guide protrusions 518 and 528, the cable 230 is spaced apart from the inner surfaces of the first and second cases 510 and 520. Accordingly, there is no friction between the cable 230 and the inner surfaces of the first and second cases 510 and 520, so when the body 100 is rotated and the cable 230 is correspondingly moved in the space defined by the first and second cases 510 and 520. Therefore, there is an effect that the cable 230 is easily moved in the space defined by the first and second cases 510 and 520.

Although the present invention was described above with reference to the embodiment, the present invention is not limited to the embodiment and it is apparent to those skilled in the art that the present invention may be changed and modified in various ways within the scope of the present invention. Further, the changes and modifications should be construed as being included in the present invention if they belong to the claims.

What is claimed is:

1. A smoke pencil with swivel device comprising:
    a body longitudinally elongated, having a space longitudinally formed therein, having a blade disposed at a longitudinal front of the space to be exposed outside, and having a coupling portion protruding from a longitudinal rear of the space;
    an operation part including a substrate disposed at a side of the space and electrically connected with the blade, an operator connected to the substrate and exposed over the space, and a cable having an end electrically connected to the substrate and another end extending out of the body through the space and the coupling portion; and
    a rotation guide comprising
        a first case, which has a first curved shape and is rotatably disposed on a side of an outer surface of the coupling portion;
        a second case, which has a second curved shape symmetrical to the first curved shape and is rotatably disposed on another side of the outer surface of the coupling portion and coupled with the first case; and
        an inflow air cannula configured to seal a first joint between a side of the coupling portion and the first case and a second joint between another side of the coupling portion and the second case,
    wherein:
        the first case comprises a first rotation guide slit and a first guide groove, which are formed on an inner surface of the first case;
        the second case comprises a second rotation guide slit and a second guide groove, which are formed on an inner surface of the second case;
        the coupling portion comprises a rotation guide protrusion, which is formed on the outer surface of the coupling portion and is configured to be inserted into and rotated along the first rotation guide slit and the second rotation guide slit; and
        the inflow air cannula comprises an insertion portion having a rod shape and configured to be inserted into the coupling portion, and a bending portion, which is positioned at a rear end of the insertion portion and positioned outside the coupling portion, and is configured to be inserted into and rotated along the first guide groove and the second guide groove.

2. The smoke pencil with swivel device of claim 1, wherein a first end portion of the first case covers a side of the outer surface of the coupling portion and a second end portion of the first case is bent downward, and
    a first end portion of the second case covers another side of the outer surface of the coupling portion and a second end portion of the second case is bent downward.

3. The smoke pencil with swivel device of claim 1, wherein the rotation guide protrusion protrudes from an outer surface of a longitudinal end portion of the coupling portion and a rotation support protrusion protrudes from an outer surface of another longitudinal end portion;
    the first rotation guide slit is formed on an inner surface of a longitudinal portion of the first case and a first rotation support slit is formed on an inner surface of another longitudinal portion of the first case so that a side of the rotation support protrusion is inserted therein; and the second rotation guide slit is formed on an inner surface of a longitudinal portion of the second case and a second rotation support slit is formed on an inner surface of another longitudinal portion of the second case so that another side of the rotation support protrusion is inserted therein.

4. The smoke pencil with swivel device of claim 3, wherein a plurality of shaved portions is formed inward from a predetermined circumference of the rotation support protrusion on an outer surface of the rotation support protrusion, and when the outer surface of the rotation support protrusion is positioned to come in contact with an inner surface of the first rotation support slit and an inner surface of the second rotation support slit, the plurality of shaved portions are spaced part from the inner surface of the first rotation support slit and the inner surface of the second rotation support slit.

5. The smoke pencil with swivel device of claim 4, wherein a contact portion protrudes from a front end of the insertion portion positioned in the coupling portion to be in contact with an inner surface of the coupling portion, and an outer surface of the insertion portion inserted in the coupling portion is spaced apart from the inner surface of the coupling portion.

6. The smoke pencil with swivel device of claim 5, wherein the contact portion is tapered as the contact portion goes away from the insertion portion.

7. The smoke pencil with swivel device of claim 4, wherein an inclined portion protruding away from a rear end of the insertion portion is formed at the rear end of the insertion portion, the bending portion is formed at an end of the inclined portion that is farthest from the rear end of the insertion portion, the inclined portion increases in diameter as the inclined portion goes away from the rear end of the insertion portion, and the inclined portion is not inserted in the first guide groove and the second guide groove so that the rear end of the insertion portion and the first and second grooves are spaced apart from each other.

8. The smoke pencil with swivel device of claim 1, wherein a first end portion of the first case and a first end portion of the second case are coupled to the coupling portion, a second end portion of the first case and a second end portion of the second case are inclined downward, a first wire guide protrusion is formed on an inner surface between the first end portion and the second end portion of the first case, a second wire guide protrusion is formed on an inner surface between the first end portion and the second end portion of the second case to be in contact with the first wire guide protrusion, and when the cable is disposed between the first case and the second case, the cable is placed over the first wire guide protrusion and the second wire guide protrusion and guided out of the first case and the second case.

\* \* \* \* \*